United States Patent [19]

Payack

[11] Patent Number: 5,210,230
[45] Date of Patent: May 11, 1993

[54] LIGNAN PROCESS

[75] Inventor: Joseph F. Payack, Somerset, N.J.

[73] Assignee: Merck & Co., Inc., Rahway, N.J.

[21] Appl. No.: 777,952

[22] Filed: Oct. 17, 1991

[51] Int. Cl.$^5$ .......................................... C07D 307/92
[52] U.S. Cl. .................................................. 549/299
[58] Field of Search .......................................... 549/299

[56] References Cited

PUBLICATIONS

Andrew Pelter, et al., J. Chem. Soc. Perkin Trans. 1 pp. 1603–1613 (1988).
R. S. Ward, Chem. J. Rev. 11, pp. 75–125 (1982).
Andrew Pelter, et al., J. Chem. Soc. Perkin Trans. I pp. 643–647 (1983).

*Primary Examiner*—Bernard Dentz
*Attorney, Agent, or Firm*—Gabriel Lopez; Joseph F. Diprima

[57] ABSTRACT

A three-step process is described for the preparation of a lignan of the formula

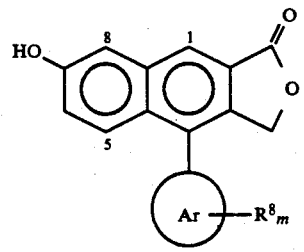

This lignan is useful as an intermediate for the preparation of anti-asthmatic pyranylphenyl hydroxyalkyl-naphthoic acids.

4 Claims, No Drawings

LIGNAN PROCESS

BACKGROUND

Pyranylphenyl hydroxyalkylnaphthoic acids are described in co-pending application, U.S. Ser. No. 834,912, filed Feb. 13, 1992, pending, which is a continuation-in-part of U.S. Ser. No. 662,535, filed Feb. 28, 1991, abandond, which are inhibitors of leukotriene biosynthesis. Said application is incorporated herein by reference and relevant portions thereof appear at the end of the Examples.

A key intermediate in the production of certain of said naphthoic acids is the lignan 7-hydroxy-3-hydroxymethyl-4-aryl-2-naphthoic acid, lactone form.

U.S. Ser. No. 662,535 teaches a multi-step, inherently low yield synthesis of this compound requiring several chromatographies.

Ward, *Chem. Soc. Rev.*, 11, 75-125 (1982) and Pelter et al., *J. Chem. Soc. Perkin Trans.*, 1603-1613 (1988), teach the synthesis of polyoxygenated lignans.

Pelter et al., *J. Chem. Soc. Perkin Trans.*, 643-649 (1983) teach a synthesis for a mono-oxygenated lignan but Scheme 5 thereof indicates no regioselectivity in the ring closure step.

SUMMARY OF THE INVENTION

An improved process has now been found for synthesizing 7-hydroxy-3-hydroxymethyl-4-aryl-2-naphthoic acid, lactone form of the formula:

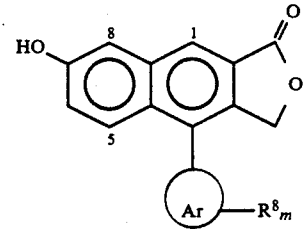

wherein:
Ar is phenyl or 1- or 2-naphthyl;
$R^8$ is halogen, lower alkyl, or lower alkoxy; and
m=0, 1, or 2.

The process comprises:
a) reacting a compound of formula 2:

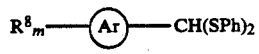

with a strong base such as t-BuLi, sec-BuLi, or n-BuLi in an ethereal solvent, adding butenolide thereto, then quenching with 3-benzyloxybenzaldehyde, all at $-100°$ to $0°$ C., to produce a compound of formula 3:

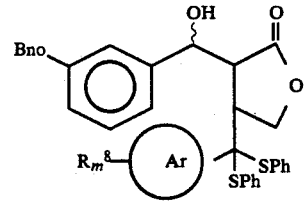

b) reacting compound 3 with a strong acid such as trifluoroacetic acid in the presence of a cation scavenger such as anisole or thioanisole at $0°-150°$ C. to produce a compound of Formula I:

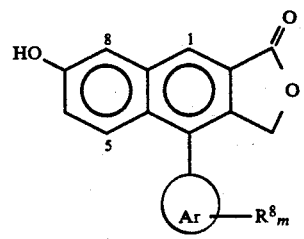

which is then, optionally, isolated as by crystallization. Advantageously, the process produces almost exclusively the 7-position isomer, requires only a final crystallization for purification, and can be run as a "one-pot" synthesis.

The improved process gives yields of 40% and requires only a final crystallization for purification.

DETAILED DESCRIPTION

The synthesis of I is based on two key steps: tandem conjugate/aldol addition to butenolide, which assembles the requisite building blocks, followed by cyclization, aromatization, and debenzylation.

Referring to Scheme 1, the thiophenol acetal 2 of arylaldehyde 1 is formed in quantitative yield using 100 mol % $BF_3.OEt_2$ as catalyst in isopropyl acetate at $0°$ C. Basic workup removes excess thiophenol. The acetal 2 is a mobile oil at RT, which slowly crystallizes upon standing. The solid can be recrystallized from hot hexanes but this is unnecessary. The anion of 2 is formed in dry THF ($[H_2O]=45$ μg/2 mL by Karl Fischer titration) at $-73°$ to $-61°$ C. by dropwise addition of n-BuLi in an ethereal solvent (such as THF, diethyl ether, or 1,2-dimethoxyethane) over 15 minutes ($N_2$ atmosphere). A yellow suspension results. After aging for 0.5 hour at $\sim -70°$ C., 2(5H)-furanone (butenolide) is added neat over 5 minutes, giving a pale yellow solution. This is aged a further 1.5 hours at $-70°$ to $-75°$ C., then a solution of 3-benzyloxybenzaldehyde in THF is added over 5 minutes, temperature being maintained below $-60°$ C. After 2 hours at $\sim -70°$ C., the reaction is quenched by addition of 200 mol % dilute aqueous acetic acid, and aqueous workup affords lactone 3 in high yield. The crude lactone could be flash chromatographed (silica, 20% EtOAc in hexanes to 23% EtOAc/hexanes) to provide pure 3 in high recovery if desired. 3 is an $\sim 2:1$ mixture of two diastereomers, which do not separate on silica, or reverse phase HPLC. The flash chromatography is difficult and can be avoided, as crude 3 is suitable as is for the next step. While the absolute stereoconfiguration of the addition has not been determined, the addition is believed to give the trans-alkylated product, with the alcohol from the second alkylation being formed with only partial stereoselectivity. In any case, the following step destroys all three stereocenters. Heating a solution of 3° to 60° C. for 1 hour in a mixture of trifluoroacetic acid/thioanisole (5:2, ~0.1 g/mL) provides I in high yield. The mechanism of this reaction is believed to involve acidic removal of thiophenol, with the resulting cation alkylating para to the benzyloxy moiety, giving the aryltetralin lactone. Subsequent aromatization and debenzylation yields I. However, the invention is not intended to be limited to this mechanism. I is isolated from the reaction mixture by removing the TFA by evaporation, flushing with toluene to azeotrope traces of TFA, then adding ethyl acetate to the resulting yellow suspension to crystallize most of the product as a pale yellow solid in good yield in greater than 90% purity.

This process efficiently produces I from arylaldehyde, with one simple crystallization providing highly purified material.

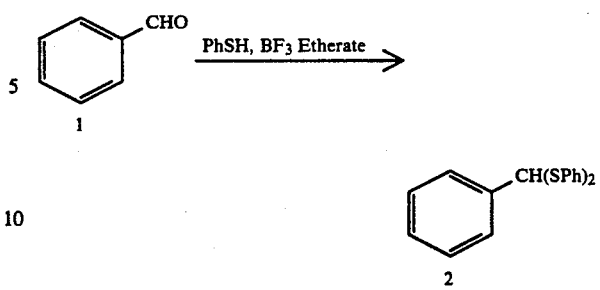

A 1-liter, 3-neck flask equipped with a mechanical stirrer, $N_2$ inlet, and thermocouple was purged with nitrogen. Benzaldehyde (16.0 g), isopropylacetate (150 mL), and thiophenol (32.5 mL) were charged to the flask, and the solution was chilled to −8° C. (ice/ethanol). $BF_3.OEt_2$ (18.5 mL) was added over 5 minutes via syringe, maintaining the temperature below 8° C. The colorless solution was aged 1.5 hours at −8° to 3°

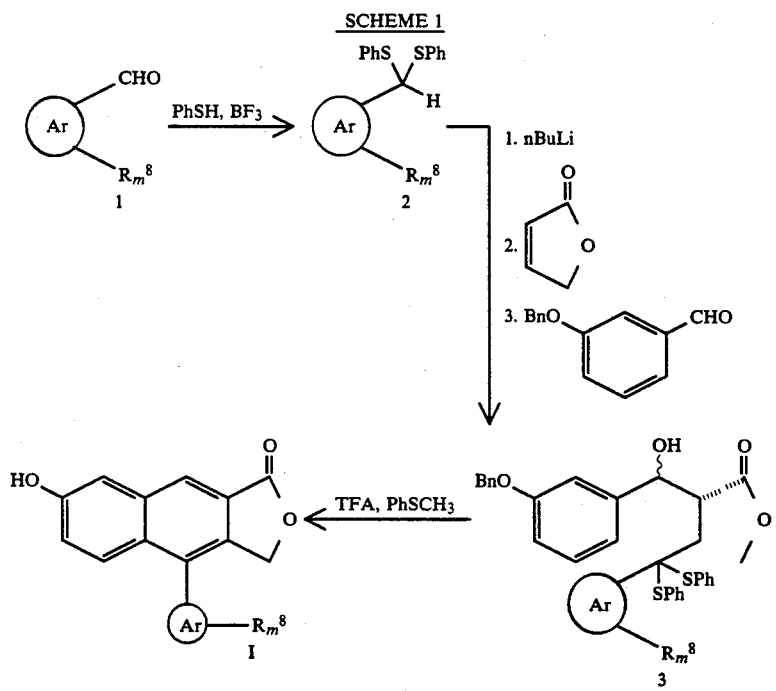

SCHEME 1

The compound of Formula I can be used in the synthesis of pyranylphenyl hydroxyalkylnaphthoic acids which are inhibitors of leukotriene biosynthesis and useful as anti-asthmatic agents. The syntheses and uses of these compounds are described below.

The invention is further defined by reference to the following example, which is intended to be illustrative and not limiting. All temperatures are in degrees celsius.

EXAMPLE 1

7-Hydroxy-3-hydroxymethyl-4-phenyl-2-naphthoic acid, lactone form

Step 1:

C. (monitored by HPLC), then was quenched by the addition of 10% aqueous $Na_2CO_3$ (100 mL) over 5 minutes (pH of aqueous phase ~7). The organic phase was washed with 10% aqueous $Na_2CO_3$ (2×50 mL) and then water (4×50 mL), then was evaporated to give 47.0 g of 2 as a colorless oil (100%, contains ~1 mol % IPAC).

HPLC Monitoring: Zorbax RX, 25 cm×6 mm; eluant=water/$CH_3CN$/$H_3PO_4$ 20/80/0.1 (v/v); flow rate=1.5 mL/min; UV detection at 270 nm; sample concentration ~0.2 mg/mL; retention times (min.)- =benzaldehyde (2.30); thiophenol acetal (4.87), 99.1 area percent.

Step 2:

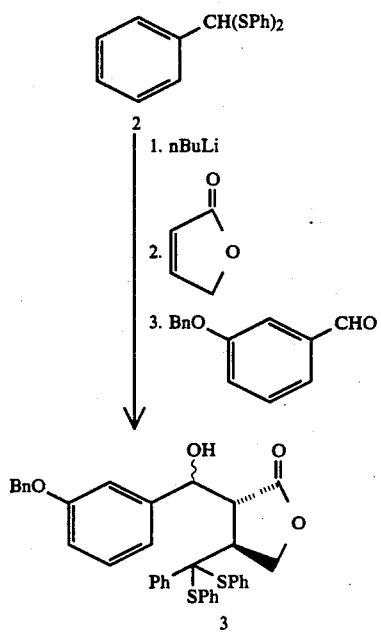

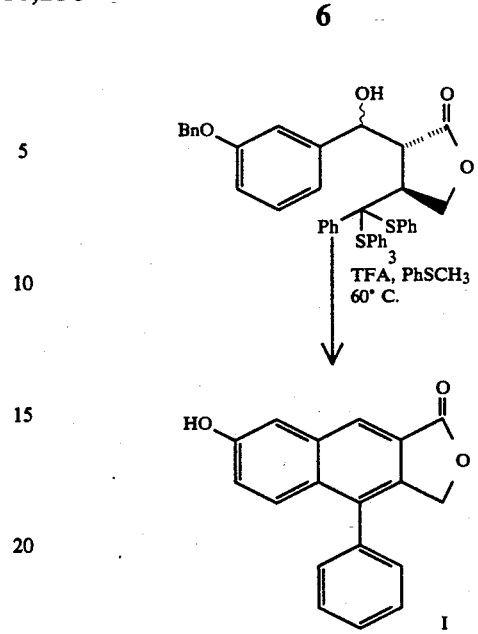

A 2-liter, 3-neck flask equipped with a mechanical stirrer, thermocouple, and addition funnel was purged overnight with nitrogen. The thioacetal from Step 1 (47.0 g) and THF (500 mL) were charged to the flask, and the colorless solution was chilled to −78° C. (dry ice, isopropanol). n-Butyl lithium (65.1 mL) was added dropwise over 15 minutes, over which time the internal temperature rose to −61° C. The resulting yellow suspension was stirred 30 minutes at ∼−70° C., then 2(5H)-furanone (13.0 mL) was added over 2 minutes (exotherm to −60° C.). The pale yellow solution was recooled to −70° C. and aged 1.5 hours at ∼−70° C., then a slurry of 3-benzyloxybenzaldehyde (32.3 g) in THF (150 mL) was added over 3 minutes, over which time the internal temperature rose to −60° C. The solution was aged a further 2 hours, then was quenched with acetic acid, maintaining the temperature below −40° C. (18.3 g of glacial acetic acid in 100 mL $H_2O$). The mixture was allowed to warm to RT, then isopropyl acetate (900 mL) and water (600 mL) were added. The aqueous phase was back extracted with isopropyl acetate (1×200 mL), then the combined organic phase was washed with saturated aqueous $NaHCO_3$ (2×200 mL) and water (3×500 mL). An emulsion formed which was broken by addition of a small amount of brine. The organic phase was evaporated in vacuo to give 96.2 g of an amber foam. The material assayed as 68 weight % 3, which gives a yield of 65.4 g (72%) of 3.

HPLC Monitoring: Conditions as given above; sample concentration ∼0.1 mg/mL; retention times (min.-)=un-reacted thiophenol acetal (4.87), 3 (5.46) 70 area % (68 weight % assay).

Step 3:

To a 2-liter, 1-neck flask containing lactone 3 from Step 2 was charged thioanisole (200 mL) and trifluoroacetic acid (500 mL). The mixture was agitated to dissolve lactone 3, then was heated (magnetic stirring) and maintained at 60° C. for 1 hour (reflux condenser, $N_2$ inlet). The dark amber solution was allowed to cool to RT, then the trifluoroacetic acid was rotary evaporated, leaving a solution of product in the remaining thioanisole. The solution was flushed with toluene (2×100 mL) to azeotropically remove traces of trifluoroacetic acid, giving a suspension of crystals in the mixture. The mixture was stirred, then ethyl acetate (325 mL) was added, giving a thick yellow suspension. After stirring 5 minutes, the mixture was filtered and the filter cake washed with ethyl acetate (2×50 mL). The pale yellow crystals were air dried overnight to give 21.2 g (mp=258°-260° C.) of 78.3 weight % assay of the title product, 16.6 g (55%), as an ethyl acetate solvate.

The mother liquor was assayed to contain an additional 4.3 g (15% yield) of the title product, giving a total assay yield of 70%.

HPLC Monitoring: Conditions as given above; retention times (min.)=starting material 3 (5.46), title product (2.37) 95.2 area %.

The following text is from U.S. Ser. No. 662,535 filed Feb. 28, 1991. This text teaches how to use the compound of Formula I of the present invention.

The products of the instant invention are used to make the following compounds:

DETAILED DESCRIPTION OF THE INVENTION

The compounds of the present invention may be represented by the following formula I:

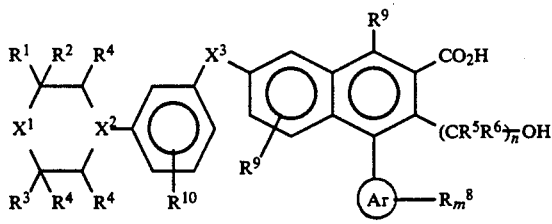

wherein:
$R^1$ and $R^5$ are independently H, OH, lower alkyl, or lower alkoxy;
$R^2$ is H, lower alkyl or together with $R^1$ forms a double bonded oxygen (=O);
$R^3$ is H, lower alkyl or together with $R^1$ forms a carbon bridge of 2 or 3 carbon atoms, said bridge optionally containing a double bond;
each $R^4$, $R^6$ and $R^7$ is independently H or lower alkyl;
$R^8$ is halogen, lower alkyl, or lower alkoxy;
each $R^9$ is independently H, halogen, lower alkyl, or lower alkoxy;
$R^{10}$ is H, halogen, lower alkyl, or lower alkoxy;
$X^1$ is O, S, S(O), S(O)$_2$, or CH$_2$;
$X^2$ is N, N(O), C(OR$^7$), or C(R$^7$);
$X^3$ is CH$_2$O, OCH$_2$, or CH$_2$CH$_2$;
Ar is phenyl or 1- or 2-naphthyl;
m is 0, 1, or 2;
n is 1 or 2;
or the pharmaceutically acceptable salts thereof.

It will be obvious to one skilled in the art that if $R^5$ is OH or lower alkoxy on the same carbon atom as the OH group of I, the elements of water or an alcohol may be lost to give an aldehyde or ketone.

Utilities

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, and 16) multiple sclerosis.

SCHEME V

The preparation of compounds of Formula I (wherein $X^3$=—CH$_2$O—) is described in Scheme V. Coupling of the phenol lactone IX with the appropriate benzyl halide XXI such as 3-[4-(4-methoxy)tetrahydropyranyl]benzyl bromide in an organic solvent such as DMF using an inorganic base such as K$_2$CO$_3$ provides the lactone XXII.

SCHEME V
PREPARATION OF FINAL PRODUCTS

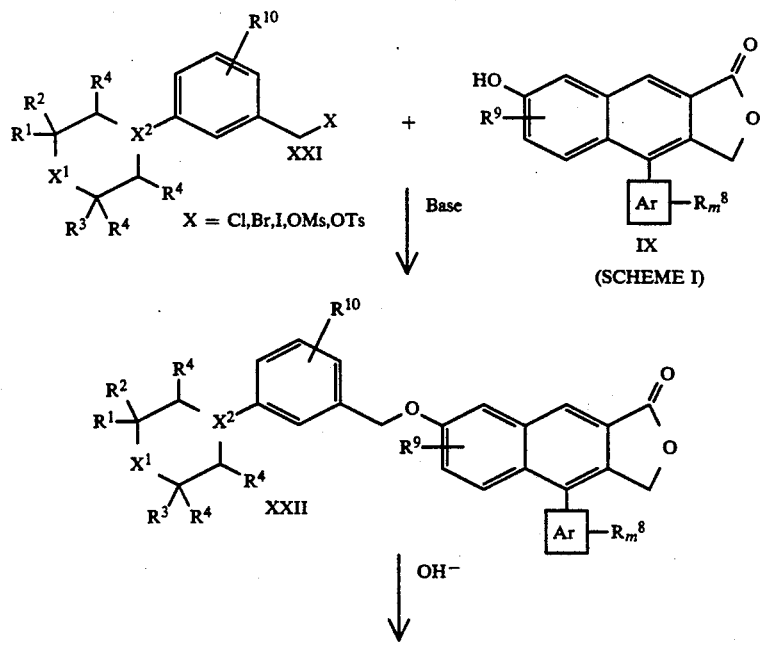

SCHEME V
PREPARATION OF FINAL PRODUCTS

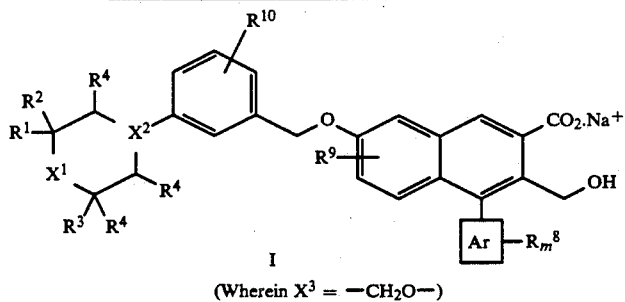

(Wherein $X^3 = -CH_2O-$)

What is claimed is:

1. A process for preparing the compound of Formula I:

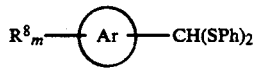

wherein:

$R^8$ is halogen, lower alkyl, or lower alkoxy;
Ar is phenyl or 1- or 2-naphthyl; and
m is 0, 1, or 2;

which comprises:

a) reacting a compound of formula 2:

$R^8{}_m$—Ar—$CH(SPh)_2$ with a strong base in an ethereal solvent, adding butenolide thereto, then quenching with 3-benzyloxybenzaldehyde all at −100° to 0° C., to produce a compound of formula 3

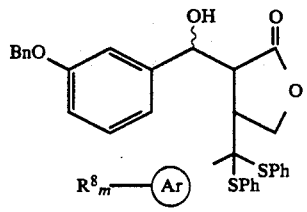

b) reacting compound 3 with a strong acid in the presence of a cation scavenger at 0°–150° C. to produce said compound of formula I.

2. The process of claim 1 wherein the base is BuLi, the acid is trifluoroacetic, and the cation scavenger is anisole or thioanisole.

3. The process of claim 1 wherein Ar is phenyl and m is 0.

4. The process of claim 1 further comprising isolating the compound of Formula I by crystallization.

* * * * *